United States Patent
Woodward et al.

(10) Patent No.: US 6,476,272 B1
(45) Date of Patent: Nov. 5, 2002

(54) ORGANOPHOSPHINES

(75) Inventors: Gary Woodward, Worcester (GB); Ranbir Singh Padda, Oxon (GB); Christian Thomas Regius, West Midlands (GB)

(73) Assignee: Rhodia Consumer Specialties Limited, West Midlands (GB)

(*) Notice: Subject to any disclaimer, the term of this patent is extended or adjusted under 35 U.S.C. 154(b) by 0 days.

(21) Appl. No.: 09/807,310

(22) PCT Filed: Oct. 21, 1999

(86) PCT No.: PCT/GB99/03482
§ 371 (c)(1),
(2), (4) Date: Jun. 18, 2001

(87) PCT Pub. No.: WO00/24752
PCT Pub. Date: May 4, 2000

(30) Foreign Application Priority Data

Oct. 24, 1998 (GB) ............................................... 9823208

(51) Int. Cl.⁷ .................................................. C07F 9/50
(52) U.S. Cl. ............................................. 568/8; 568/17
(58) Field of Search ........................................ 568/8, 17

(56) References Cited

U.S. PATENT DOCUMENTS

| | | | |
|---|---|---|---|
| 2,803,597 A | * | 8/1957 | Stiles et al. |
| 3,257,460 A | | 6/1966 | Gordon |
| 4,073,810 A | * | 2/1978 | Hestermann et al. |
| 5,003,108 A | * | 3/1991 | Stelzer et al. .................. 568/8 |
| 5,354,918 A | * | 10/1994 | Ohsaki et al. ................. 568/8 |
| 5,866,720 A | * | 2/1999 | Layman, Jr. et al. ......... 568/17 |

FOREIGN PATENT DOCUMENTS

| | | |
|---|---|---|
| CA | 2 086 285 A | 6/1994 |
| GB | 2 258 654 A | 2/1993 |

OTHER PUBLICATIONS

Hellmann H., "Hydroxymethyl–Phosphine, Hydroxymethyl–Phosphoniumsalze und Clormethyl–Phosphoniumsalze" Justus Liebigs Annalen Der Chemie., vol. 659, 1962, pp. 49–63, XP002130429 Verlag Chmie GmbH. Weinheim., DE Issn.: 0075–4617.

* cited by examiner

*Primary Examiner*—Jean F. Vollano
(74) *Attorney, Agent, or Firm*—Frishauf, Holtz, Goodman & Chick, P.C.

(57) ABSTRACT

Organophosphines of the formula $(R)_aP(H)_{3-a}$ (where R is C1–C20 alkyl, alkenyl, alkaryl or styryl and a is 1, 2, or 3) are produced by (i) reacting a tris(hydroxyorgano)phosphine (THP) with an organic halogen containing compound; (ii) reacting the product of (i) with a base; (iii) removing aldehydes from the product of (ii) and adding an organic phase, followed by distillation or phase-separation to obtain the desired product.

16 Claims, No Drawings

ORGANOPHOSPHINES

This application is a U.S. National Phase Application under 35 USC 371 of International Application PCT/GB99/03482 (published in English) filed Oct. 21, 1999.

This invention relates to a method for the production of primary, secondary or tertiary phosphines and to phosphines obtained from the aforesaid method.

In particular, the present invention relates to the preparation of organophosphines of the formula $R_{(a)}PH_{(3-a)}$ where R is an organic group and a is 1, 2 or 3.

Organophosphines are used as intermediates in the synthesis of a wide range of organophosphorus fine chemicals, including pesticides and pharmaceuticals. One conventional method of preparing alkylphosphines involves the use of high-pressure phosphine. This is a hazardous operation and requires a special plant which is expensive to install, expensive to maintain and expensive to operate safely. Moreover, this technology is used to manufacture tri-alkyl phosphines. Primary and secondary phosphines are not readily accessible by this method.

A more selective alkylation of phosphine can be achieved by reacting Grignard reagents with phosphorus halides, followed by reduction with, for example, lithium aluminium hydride. However, this approach is generally unsuitable for commercial production on account of the high cost of the reagents.

Primary and secondary phosphines can also be prepared by thermal disproportionation of alkyl- or dialkyl-phosphonous acids. Such routes have low yields.

We have now discovered that primary, secondary or tertiary phosphines can be prepared by way of a convenient reaction using relatively low cost reagents and standard pressures. In particular we found that the reaction can be made to yield specific mono-, di-, or tri-alkyl phosphines in high yield, or desired mixtures of the phosphines.

Accordingly, the present invention provides a method for the production of a primary, secondary or tertiary phosphine having the general formula $(R)_aP(H)_{3-a}$, where a is 1, 2 or 3, in which the method comprises the following stages:

(i) reacting a tris(hydroxyorgano)phosphine (THP) with an organic halogen-containing compound;

(ii) reacting the product of stage (i) with a base;

(iii) removing aldehydes from the product of stage (ii) and adding an organic phase, followed by distillation or phase-separation to obtain the desired phosphine.

Preferably, the THP has its hydroxy group on the carbon atom which is joined to the phosphorus atom.

Preferably, the removal of aldehydes from the product of stage (ii) is achieved by the addition of sodium sulphite.

The present invention also provides a primary, secondary or tertiary phosphine made by the method described in the immediately-preceding paragraph. Such phosphines include, for example, 1,2-diphosphino-ethane, diethylphosphine and tri-n-butyl phosphine.

Preferably, in stage (i), there is present a stoichiometric excess of the organic halogen-containing compound, relative to the THP. For example, the halogen-containing compound may be present in an amount of up to 10:1, for example 2:1 to 3:1, relative to the THP.

Stage (i) is preferably carried out at a temperature of less than 90°, at ambient pressure. Stage (i) may be carried out in an inert (e.g. nitrogen or argon) atmosphere. Stage (i) is preferably carried out in the presence of a solvent. The solvent may be water or a water/alcohol mixture, sufficient to solubilise the organic halogen-containing compound and to achieve a practical reaction-rate.

The organic halogen-containing compound may suitably have the general formula $R(X)_n$, where R represents an alkyl, alkenyl, alkaryl, alkynyl or styryl group of from 1 to 20 (preferably 2 to 8) carbon atoms, X represents a halogen (e.g. chlorine, bromine or iodine—preferably bromine) atom and n is a whole number of from 1 to 4, the group R having at least one aliphatic carbon atom adjacent the or each halogen atom.

For example, the organic halogen-containing compound may be ethyl bromide, butyl bromide, 1,2-dibromo-ethane or 1,3-dibromopropane.

The group R may further include one or more ether-or amino-linkages. The base used in stage (ii) may be, for example, sodium hydroxide or potassium hydroxide.

The aldehyde-removing agent used in stage (iii) may be, for example, sodium sulphite. During stage (iii), the pH of the reaction mixture is preferably maintained at 6.0 to 8.0 by the addition of an acid such as hydrochloric acid or phosphoric acid or a suitable organic acid such as acetic acid.

The organic phase added to the reaction mixture during stage (iii) may be a mineral oil (such as paraffin oil) or a petroleum ether of suitable boiling-point range (for example 100–120° C.).

While the reaction which is the subject of the present invention has been described herein with particular reference to the use a tris(hydroxyogano) phosphine (THP) as the starting material, it is also possible to obtain the THP in situ by reacting a tetrakis(hydroxyalkyl)phosphonium salt with a base. For example, tris(hydroxymethyl)phosphine can be produced in situ by reacting tetrakis(hydroxymethyl) phosphonium chloride (THPC) or tetrakis(hydroxymethyl) phosphonium sulphate (THPS) with sodium hydroxide.

The invention will be illustrated by way of the following examples.

EXAMPLE 1

(1A) Preparation of tri-n-butylphosphine (First Method)

This reaction was carried out in a nitrogen atmosphere, all reactants having been purged with nitrogen before use.

(a) A 12-liter reactor was charged with tetrakis (hydroxymethyl)phosphonium chloride (986 g, 4 mole) and ethanol (838 g, 18 mole) and purged with nitrogen for 15 minutes.

(b) A solution of sodium hydroxide (160 g, 4 mole) in water (160 g) was added to the reactor over 1.5 hours, keeping the temperature below 20° C. and the pH below 8.

At the end of this addition, N.M.R. analysis of the product indicated:

| | |
|---|---|
| tetrakis(hydroxymethyl)phosphonium chloride | 5.2% |
| tetrakis(hydroxymethyl)phosphonium oxide | 0.7% |
| tris(hydroxymethyl)phosphine | 94.1% |

(c) n-Butyl bromide (1640 g, 12 mole) was added, the mixture heated to 65° C. and held at that temperature for 4 hours. The mixture was then cooled to the ambient temperature, when N.M.R. analysis showed:

| | |
|---|---|
| tetrakis(hydroxymethyl)phosphonium chloride | 15.7% |
| butylphosphonium compounds | 78.3% |
| tris(hydroxymethyl)phosphine | 6% |

(d) A further solution of sodium hydroxide (160 g, 4 mole) in water (160 g) was added to the reactor over 1.5 hours, keeping the temperature below 20° C. and the pH below 8. The mixture was then heated to 65° C. for 5 hours. N.M.R. analysis of the product showed:

| | |
|---|---|
| tris(hydroxymethyl)butylphosphonium ion | 16.8% |
| bis(hydroxymethyl)dibutylphosphonium ion | 54.3% |
| mono(hydroxymethyl)tributylphosphonium ion | 22% |
| tris(hydroxymethyl)phosphine | 2% |
| tetrakis(hydroxymethyl)phosphonium oxide | 4% |

(e) A further solution of sodium hydroxide (80 g, 2 mole) in water (80 g) was added over 1 hour, keeping the temperature below 20° C.
The mixture was then heated to 65° C. for 3 hours. N.M.R. analysis showed:

| | |
|---|---|
| tris(hydroxymethyl)butylphosphonium ion | 3.8% |
| bis(hydroxymethyl)dibutylphosphonium ion | 41.4% |
| mono(hydroxymethyl)tributylphosphonium ion | 47.5% |
| tetrakis(hydroxymethyl)phosphonium oxide | 4.2% |

(f) The reaction mixture obtained from (e) above was subjected to vacuum-stripping to remove volatile organic components. Water (2.5 l) and petroleum ether (250 ml, b.p. 100–120° C.) were added to the mixture to produce a two-phase system, followed by solid sodium sulphite (2000 g) which caused the pH of the mixture to rise to 11.5. The pH was reduced to 6.5 by the addition of concentrated hydrochloric acid over 3 hours and the mixture was then heated to 45° C. The pH was maintained at 6.5 over the next 18 hours, more hydrochloric acid being added as required.
N.M.R. analysis showed:

| | |
|---|---|
| hydroxymethylphosphines | 0.9% |
| tributylphosphine | 50.2% |
| dibutylphosphine | 45% |
| monobutylphosphine | 3.2% |

(g) The phases were separated and the organic phase transferred to a pressure-reactor, which was pressurised with butene to 15–20 p.s.i. An azo-initiator, used as a source of free radicals, was pumped into the reactor each hour for about 20 hours. The butylation stage reduced the amount of dibutylphosphine from 45% to less than 1%.
(h) After vacuum-stripping to remove volatile organic components, the tributylphosphine was distilled under vacuum. The yield (based on phosphorus) was about 65% of theoretical and the purity of the product was found to be over 98%.

(1B) Preparation of tri-n-butyl phosphine (Second Method)

(a) A 5-liter jacketed reactor was charged with tetrakis-(hydroxymethyl) phosphonium chloride (507 g, 2 mole) and ethanol (500 ml) and purged with nitrogen for 15 minutes.
(b) A solution of sodium hydroxide (80 g, 2 mole) in water (80 g) was added to the reactor over 1.5 hours, keeping the temperature below 20° C. and the pH below 8.
(c) n-Butyl bromide (685 g, 5 mole) was added over 1 hour while heating to 65° C. then heating for a further 3 hours. At the end of this time, N.M.R. analysis showed:

| | |
|---|---|
| tetrakis(hydroxymethyl)phosphonium chloride | 15.4% |
| tetrakis(hydroxymethyl)phosphonium oxide | 0.7% |
| butylphosphoniums | 74% |
| tris(hydroxymethyl)phosphine | 9% |

(d) A further solution of sodium hydroxide (120 g, 3 mole) in water (120 g) was charged to a dropping-funnel and added to the mixture over 5 hours at 65° C., the pH being kept below 9 throughout. Heating was continued for a further 1.5 hours.
N.M.R. analysis showed:

| | |
|---|---|
| tetrakis(hydroxymethyl)phosphonium oxide | 4.5% |
| mono(hydroxymethyl)tributylphosphonium ion | 16.6% |
| bis(hydroxymethyl)dibutylphosphonium ion | 72.2% |
| tris(hydroxymethyl)butylphosphonium ion | 0.3% |
| tris(hydroxymethyl)phosphine | 5% |

(e) After vacuum-stripping to remove volatile organic components, water (1.2l) and petroleum ether 120 ml, b.p. 100–120° C., were added to the mixture to produce a two-phase system, followed by solid sodium sulphite (1008 g) at 30° C., causing the pH of the mixture to rise to 10. Concentrated hydrochloric acid was added, in 5-ml portions, over the next 12 hours. The final pH of the mixture was 6.2. At this stage, N.M.R. analysis of the organic phase showed:

| | |
|---|---|
| tributylphosphine | 15.6% |
| dibutylphosphine | 71.4% |
| monobutylphosphine | 5.5% |
| mono(hydroxymethyl)dibutylphosphine | less than 1% |

The aqueous phase was removed from the reactor and the organic phase washed twice with water before being transferred to a pressure reactor.
(f) Pressurisation with butene was carried out as described in the corresponding stage of Example 1A (above). The yield (based on phosphorus) was about 75% of theoretical and the purity of the product was found to be over 98%.

EXAMPLE 2

Preparation of diethylphosphine (a) Tetrakis(hydroxymethyl)phosphonium chloride (600 g, 3 moles) and ethanol (600 ml, 13 mole) were charged to a 5-liter jacketed reactor. A solution of sodium hydroxide (97 g, 2.4 mole) in water (97 g) was added over 70 minutes, keeping the pH of the mixture below 8 and the temperature below 20° C.
(b) Ethyl bromide (793 g, 7 mole) was added and the mixture heated to about 40° C. for 3 hours. The pH of the mixture dropped slowly during that time, the final pH being 7.21.
(c) A further solution of sodium hydroxide (123 g. 3 mole) in water (123 g) was charged to a dropping funnel, sufficient of the solution being added to the reactor to raise the pH to 7.5. This pH was maintained for 1 hour. The pH was raised, by the addition of sodium hydroxide solution, by 0.5 per hour, so that after a further 6 hours the pH of the mixture was 10.5. At this stage, N.M.R. analysis showed:

| mono(hydroxymethyl)triethylphosphonium ion | 13.5% |
| bis(hydroxymethyl)diethylphosphonium ion | 75.5% |
| tris(hydroxymethyl)ethylphosphonium ion | 2.8% |
| tris(hydroxymethyl)phosphine | 7% |
| tetrakis(hydroxymethyl)phosphonium oxide | less than 1% |

(d) Unreacted ethyl bromide and ethanol were removed under vacuum at 40° C.

(e) Water (500 ml) and mineral oil (250 ml) were added to the reactor to form a two-phase system. A distillation apparatus was fitted to the reactor. Solid sodium sulphite (1000 g) was added, the pH of the mixture rising to 10.8. The pH was reduced to 7 by the gradual addition of concentrated hydrochloric acid. The mixture was then heated to 115° C. to distil out a mix of water and diethylphosphine. The pH was kept at 8 by addition of further hydrochloric acid to the reactor. The total time for this stage was about 7 to 14 hours. The yield (based on phosphorus) was about 50% of theoretical.

Analysis of the final product showed it to be a mixture comprising:

| diethylphosphine and | 85% |
| triethylphosphine | 15% |

EXAMPLE 3

Preparation of 1,2-diphosphinoethane 1,2-diphosphinoethane (BPE) was prepared from tetrakis(hydroxmethyl)phosphonium chloride (THPC) as follows:

All reactions were carried out under a nitrogen atmosphere in a 2-liter round-bottomed flask.

(a) THPC (200 g aqueous solution, 154.0 g actives, 0.808 moles) was charged to the reaction vessel, together with ethanol (600 ml). Sodium hydroxide solution (29.1 g, dissolved in 30.0 g water) was added slowly via a dropping funnel, keeping the temperature below 27° C. This generated tris(hydroxymethyl)phosphine (THP). 1,2-Dibromoethane (50.7 g, 0.27 moles) was added and the reaction mixture heated at reflux for 4.5 hours. A further addition of sodium hydroxide solution (10.0 g, in 10.0 g water) was made at this point and the reaction mixture heated for a further 6.5 hours. The ethanol was then stripped out under vacuum, leaving a viscous residue. $^{31}$P N.M.R. analysis of the residue showed 32.2 mole % conversion to the desired phosphonium intermediate.

(b) The residue from (a) above was diluted with water (250 ml, de-gassed) and the pH adjusted to 7.5. Petroleum ether (300ml) and solid sodium sulphite was added (408.0 g, 3.23 moles) and the pH of the reaction mixture was re-adjusted back to 7.0 by the addition of concentrated hydrochloric acid. The mixture was stirred and heated at 40° C. for 12 hours, further concentrated hydrochloric acid (ca. 40 ml) being added slowly in order to maintain the pH between 6.5–7.0 $^{31}$P N.M.R. analysis of the petroleum ether layer at this point showed the presence of BPE product.

EXAMPLE 4

Synthesis of diethyl phosphine

All reactions were carried out in a 10-liter jacketed reactor fitted with a dropping-funnel, a temperature probe, a condenser and a glass pH-electrode. The reactions were carried out under a nitrogen atmosphere.

(a) THPC (1500 g of 75% w/w aqueous solution, 6 moles) and ethanol (1500 ml) were charged to the reactor. A solution of sodium hydroxide (243 g, 6 moles) in water (243 g) was added to the reactor over about 2 hours, keeping the pH below 8 and the temperature below 25° C.

(b) Ethyl bromide (2000 g, 18 moles) was added. The mixture was heated to about 40° C. for 3 to 4 hours, then left overnight.

(c) The mixture was re-heated to 40° C. A solution of sodium hydroxide (310 g, 7.7 moles) in water (310 g) was charged to the dropping funnel and sufficient of this solution added to the contents of the reactor to bring the pH to 7.5. This pH was maintained for 45 minutes, then raised (by addition of the sodium hydroxide solution) to 8.0 for a further 45 minutes, then to 8.5 for 45 minutes. The addition was continued at the same rate until all the sodium hydroxide solution had been added. At that stage (with the pH about 10.5) heating was continued for a further 2 hours. A distillation apparatus was fitted to the reactor: ethanol and any remaining ethyl bromide were removed under vacuum with the aid of a TEFLON®-lined pump.

$^{31}$P N.M.R. analysis at this time showed:

| mono(hydroxymethyl)triethylphosphonium ion | 20% |
| bis(hydroxymethyl)diethylphosphonium ion | 75% |
| tris(hydroxymethyl)ethylphosphonium ion | 5% |

(d) Water (2500 ml) and mineral oil (600 ml) were added to the mixture, followed by solid sodium sulphite (2500 g, 20 moles). The pH of the mixture rose to about 11 and was then slowly lowered by addition of concentrated phosphoric acid. The mixture was then heated to 115° C. to distil out an azeotropic mixture of water and diethyl phosphine. Phosphoric acid was added to the reactor whenever the pH of the contents rose above 8. This stage took 2 days to complete. The phases in the receiver were separated, producing a mixture comprising:

| diethylphosphine | about 75% |
| triethylphosphine | about 15% |
| mono(hydroxymethyl)diethylphosphine | |
| bis(hydroxymethyl)ethylphosphine | about 10% |

The weight of the mixture was 500 g, corresponding to a yield of about 70% theoretical.

(e) Acetic acid (25%, 500 ml) was added to the receiver and stirred for 10 minutes. The water layer was removed and the organic layer washed with water (500 ml).

$^{31}$P N.M.R. analysis of the organic layer showed the purity of the diethyl phosphine to be greater than 95%.

EXAMPLE 5

Coupling of diethyl phosphine

Route (I)

All reactions were carried out under an argon atmosphere in a 5-liter jacketed reactor fitted with a dropping funnel, a temperature probe and a condenser.

(A) 95% pure diethylphosphine (400 g, 4.2 moles) and t-butylmethyl ether (1000 ml) were charged to the reactor and cooled to below 0° C. Butyllithium (2620 ml, 4.2 moles) in hexanes (1.6 molar, ex Aldrich) was added over 2–3 hours, the temperature being kept below 0° C. A yellow, slightly cloudy solution was obtained. Some of the mixture was quenched with $D_2O$ in an N.M.R. tube, to check conversion. More butyllithium was added as required.

(b) 1,2-dichloroethane (205 g, 2.1 moles) was diluted with t-butylmethyl ether (500 ml) and slowly added to the reactor over 2–3 hours, the temperature being kept below 0° C. A white solid formed during this stage. The mixture was heated to reflux for 1 hour, then quenched with water (500 ml).

(c) To remove the unwanted by-product (tetraethyl diphosphine, about 10% of the mixture) air was admitted to the reactor head space (4–5 times, checked by $^{31}P$ N.M.R.). The water layer was removed, then the solvents were distilled off. The remaining slightly yellow oil was washed with water (500 ml) and then transferred to a distillation apparatus fitted with a fractionating column and distilled as described in Example 4 above. The product consisted of a colourless liquid (230 g, corresponding to a yield of 53% theoretical).

Route (II)

All reactions were carried out under a nitrogen atmosphere in a 5-liter jacketed reactor fitted with a dropping funnel, a temperature probe and a condenser.

(a) 95% pure diethyl phosphine (400 g, 4.2 moles) was charged to the reactor and heated to reflux (78° C.). 1,2-dibromoethane (244 g, 1.9 moles, i.e. 10% excess of diethylphosphine) was charged to the dropping funnel and then added, over 4 hours, to the refluxing mixture. The liquid turned cloudy after 30 minutes and became more and more viscous over the addition period. The viscous slurry was heated to 78° C. for a total period of 3 days.

(b) The slurry was cooled to 70° C. and water (11) added. $^{31}P$ N.M.R. showed:

tetra-ethyl-bis phosphonoethyl-phosphonium ion 72%

A pH-probe was fitted to the reactor and sodium hydroxide solution added slowly until the pH of the contents reached 10. Three layers had formed.

(c) $^{31}P$ N.M.R. showed the bottom layer to contain both cyclic and long-chain polymers. The middle layer was found to comprise mainly a phosphonium species of formula:

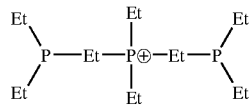

where Et=ethyl. The top layer contained the desired tetra-ethyl-bisphosphonoethyl-phosphonium ion (TEBPE) together with diethylphosphine. This layer was removed and weighed, giving 530 g, which corresponds to 442 g TEBPE (68% yield of theoretical).

(d) The top layer was transferred to a vacuum-distillation apparatus fitted with a Perkin-triangle fractionating column. The diethylphosphine was distilled off at atmospheric pressure. A vacuum was then applied by means of an oil-pump and the product distilled off at 90–95° C. as a colourless liquid.

EXAMPLE 6

Synthesis of dibutyl phosphine

THPC (75% aqueous solution, 500 g, 2 moles) and ethanol (300ml) were charged to a 5-liter reactor. A solution of sodium hydroxide (79 g) in water (79 g) was added over 30 minutes, keeping the temperature below 30° C. and the pH below 8. Butyl bromide (620 g, 4.5 moles) was added and the mixture heated to 65° C. for 4 hours. Sodium hydroxide (102 g) in water (102 g) was charged to a dropping funnel and added in portions to the contents of the reactor, increasing the pH by 0.5 every 45 minutes. After addition of the sodium hydroxide solution, heating was continued for 2 hours. $^{31}P$ N.M.R. at this stage showed about 80% of the phosphonium species of formula:

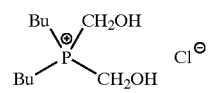

where Bu=butyl

The volatile organic components were stripped using a TEFLON®-lined vacuum pump. Water (1l), mineral oil (300ml) and sodium sulphite (1000 g, 8 moles) were then added, leading to a pH of 10.9. Phosphoric acid was added until the pH was about 7. A distillation apparatus was fitted to the reactor and the contents heated to 115° C. Two layers slowly formed in the receiver flask. After 6 hours, $^{31}P$ N.M.R showed that no phosphonium species remained in the reactor. $^{31}P$ N.M.R. of the top layer in the receiver flask showed it to be 75% dibutylphosphine, the remainder comprising monobutyl phosphine, tributyl phosphine and some hydroxymethyl species.

The layers were separated and the organic layer washed with 75% acetic acid. This removed all the tributylphosphine, leaving behind about 7.5% monobutyl phosphine. The yield of dibutylphosphine was 126 g, corresponding to 40% of theoretical.

EXAMPLE 7

Coupling of di-n-butylphosphine with 1,3-dibromopropane

Dibutylphosphine (126 g, 0.86 moles) was heated to 1000° C. and dibromopropane (0.35 moles, 10% excess of the phosphine) was added slowly over 6 hours. The solution became cloudy and very viscous. After standing overnight a white solid was obtained. This was melted and stirred at 110° C. for 1 day. $^{31}P$ N.M.R. showed mainly one signal (at about 12 ppm), most probably the desired bisphosphonium salt. The next day, the viscous product was heated to 110° C. for 4 hours, after which water (1000 ml) was added to give a two-layer system.

$^{31}P$ N.M.R. analysis of the top layer showed it to consist mainly of dibutylphosphine. This layer was removed and weighed, giving 21 g dibutylphosphine, equivalent to a recovery of about 17%.

Sodium hydroxide (40 g) in water (40 g) was added to give a three-layer system. $^{31}P$ N.M.R. showed the top layer to be the desired product. The middle layer was found to contain one polymeric phosphonium species, probably a species having the formula:

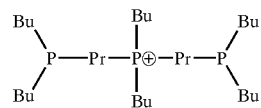

where Bu=butyl and Pr=propyl, together with some of the product. As it was impossible to separate these two species, the whole of the middle layer was discarded.

The top layer was weighed and found to contain 85 g of tetrabutyl bisphosphino propane (92% purity as shown by $^{31}$P N.M.R.) corresponding to a yield of 67% of theoretical.

What is claimed is:

1. A method for the production of a primary, secondary or tertiary phosphine having the formula $(R)_aP(H)_{3-a}$ where R is an organic group and a is 1, 2 or 3, wherein said method comprises the following stages:

(i) reacting a tris(hydroxyorgano)phosphine (THP) with an organic halogen-containing compound, of formula $R(X)_n$ where:

R is selected from the group consisting of $C_1$ to $C_{20}$ alkyl, alkenyl, alkynyl, alkaryl and styryl;

X represents a halogen atom;

n is a whole number of from 1 to 4 and said R includes at least one aliphatic carbon atom adjacent each said halogen atom;

said stage (i) being carried out at a temperature of less than about 90° C. and at ambient pressure and in the presence of a solvent;

(ii) reacting the product of stage (i) with a base;

(iii) thereafter adding, to the resulting product of stage (ii), sufficient of an acid to maintain a pH of 6 to 8, removing aldehydes from said product of stage (ii) and adding to said product a material to form a discrete organic phase, followed by distilling or phase-separation to obtain said primary, secondary or tertiary phosphine.

2. The method of claim 1, wherein each hydroxy group present in said THP is attached to the carbon atom which is joined to the phosphorus atom of said THP.

3. The method of claim 1, wherein said organic halogen-containing compound is present in said reaction in a stoichiometric excess amount of up to 10:1 by equivalent weight, relative to said THP.

4. The method of claim 1, wherein said organic halogen-containing compound is present in said reaction in an amount of 2:1 to 3:1 by equivalent weight, relative to said THP.

5. The method of claim 1, wherein said stage (i) is carried out in an inert atmosphere.

6. The method of claim 5, wherein said inert atmosphere consists essentially of a gas selected from the group consisting of nitrogen and argon.

7. The method of claim 1, wherein said solvent is selected from the group consisting of water and water/alcohol mixtures, said solvent being present in an amount sufficient to solubilise said organic halogen containing compound.

8. The method of claim 1, wherein said group R contains from 2 to 8 carbon atoms.

9. The method of claim 1, wherein said atom X is selected from the group consisting of chlorine, bromine and iodine.

10. The method of claim 1, wherein said organic halogen-containing compound is selected from the group consisting of ethyl bromide, butyl bromide, 1,2-dibromo-ethane and 1,3-dibromo-propane.

11. The method of claim 1, wherein said group R contains at least one ether-linkage or at least one amino-linkage.

12. The method of claim 1, wherein, in said stage (iii), said removal of aldehydes is achieved by adding sodium sulphite.

13. The method of claim 1, wherein, in said stage (iii) said acid is selected from the group consisting of hydrochloric acid, phosphoric acid and acetic acid.

14. The method of claim 1, wherein, in said stage (iii), said material to form a discrete organic phase consists essentially of a substance selected from the group consisting of mineral oils and petroleum ethers.

15. The method of claim 1, wherein said THP is first obtained by reacting a tetrakis(hydroxyalkyl)phosphonium salt with a base.

16. A method of claim 12, wherein said tetrakis (hydroxymethyl phosphonium salt is selected from the group consisting of tetrakis(hydroxymethyl)phosphonium chloride and tetrakis(hydroxymethyl)phosphonium sulphate.

* * * * *